(12) United States Patent
Overes et al.

(10) Patent No.: US 10,363,144 B2
(45) Date of Patent: Jul. 30, 2019

(54) EXPANDABLE SPINAL IMPLANT

(71) Applicant: 41MEDICAL AG, Bettlach (CH)

(72) Inventors: Tom Overes, Langendorf (CH); Robert Frigg, Bettlach (CH)

(73) Assignee: 41MEDICAL AG, Bettlach (CH)

( * ) Notice: Subject to any disclaimer, the term of this patent is extended or adjusted under 35 U.S.C. 154(b) by 226 days.

(21) Appl. No.: 15/515,122

(22) PCT Filed: Jul. 16, 2015

(86) PCT No.: PCT/CH2015/000106
§ 371 (c)(1),
(2) Date: Mar. 28, 2017

(87) PCT Pub. No.: WO2016/049784
PCT Pub. Date: Apr. 7, 2016

(65) Prior Publication Data
US 2017/0209284 A1    Jul. 27, 2017

(30) Foreign Application Priority Data
Sep. 29, 2014 (CH) ........................................ 1470/14

(51) Int. Cl.
*A61F 2/44* (2006.01)
*A61F 2/46* (2006.01)
*A61F 2/30* (2006.01)

(52) U.S. Cl.
CPC ............ *A61F 2/4455* (2013.01); *A61F 2/447* (2013.01); *A61F 2/4425* (2013.01);
(Continued)

(58) Field of Classification Search
CPC ........ A61F 2/44; A61F 2/4455; A61F 2/4425; A61F 2/447; A61F 2/46; A61F 2/4611
See application file for complete search history.

(56) References Cited

U.S. PATENT DOCUMENTS 9,492,288 B2* 11/2016 Wagner .................. A61F 2/447
2012/0310350 A1 12/2012 Farris et al.
(Continued)

FOREIGN PATENT DOCUMENTS

WO    2005/112834 A2    12/2005
WO    2014/091028 A1     6/2014

*Primary Examiner* — Christopher J Beccia
(74) *Attorney, Agent, or Firm* — Maschoff Brennan

(57) ABSTRACT

An expandable spinal implant assembly is configured to be inserted between two adjacent vertebral bodies. The expandable spinal implant assembly includes a substantially hollow first body with a first superior endplate with a first top inside face and a first inferior endplate with a first bottom inside face. The first superior endplate and the first inferior endplate are connected together by a lateral wall. At least one strut is arranged within said first body, connecting the first top inside face with the first bottom inside face, said strut including a first threaded through bore. The assembly further includes a substantially hollow second body with a second superior endplate and a second inferior endplate, said second body inserted within said first body. A central screw with a first end including a ball-head and a drive, said central screw further having a threaded shaft is engaged within said first threaded through bore.

11 Claims, 18 Drawing Sheets

(52) U.S. Cl.
CPC ............ *A61F 2/4611* (2013.01); *A61F 2/446* (2013.01); *A61F 2002/3055* (2013.01); *A61F 2002/3082* (2013.01); *A61F 2002/30166* (2013.01); *A61F 2002/30331* (2013.01); *A61F 2002/30507* (2013.01); *A61F 2002/30836* (2013.01); *A61F 2002/448* (2013.01); *A61F 2002/4475* (2013.01); *A61F 2002/4623* (2013.01); *A61F 2250/0009* (2013.01); *A61F 2250/0065* (2013.01)

(56) References Cited

U.S. PATENT DOCUMENTS

| | | |
|---|---|---|
| 2013/0103156 A1 | 4/2013 | Packer et al. |
| 2013/0190876 A1* | 7/2013 | Drochner ............... A61F 2/442 623/17.16 |
| 2014/0180419 A1* | 6/2014 | Dmuschewsky ....... A61F 2/442 623/17.16 |

* cited by examiner

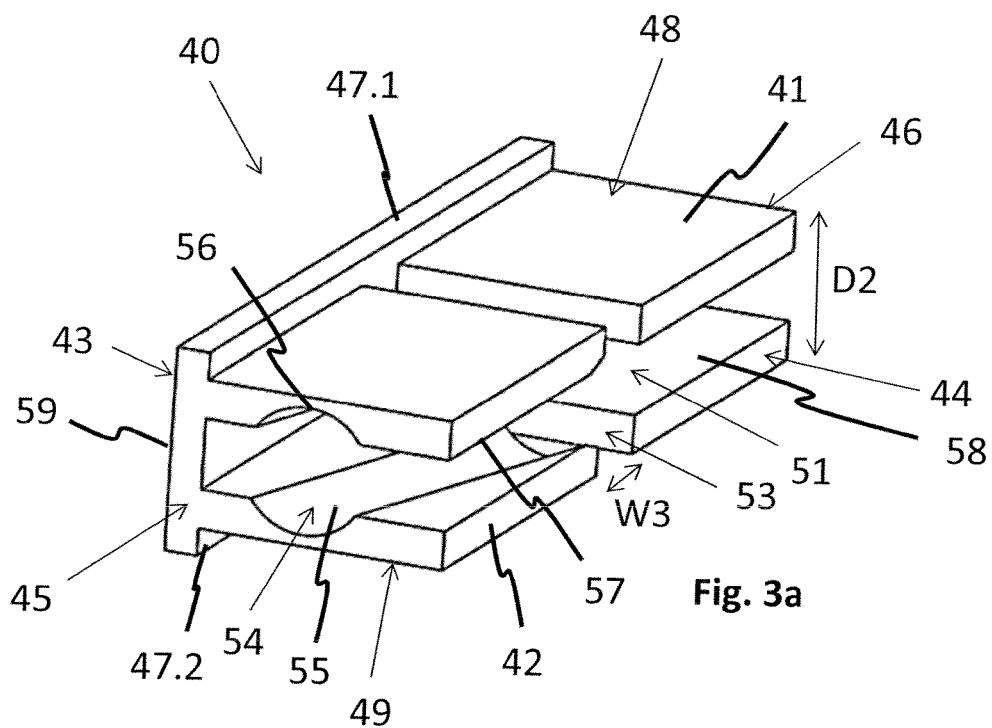
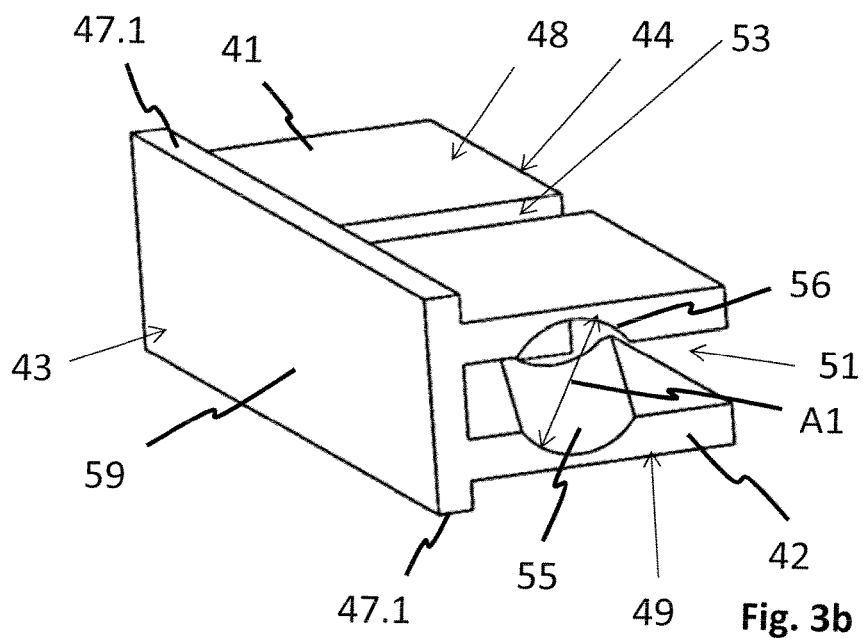

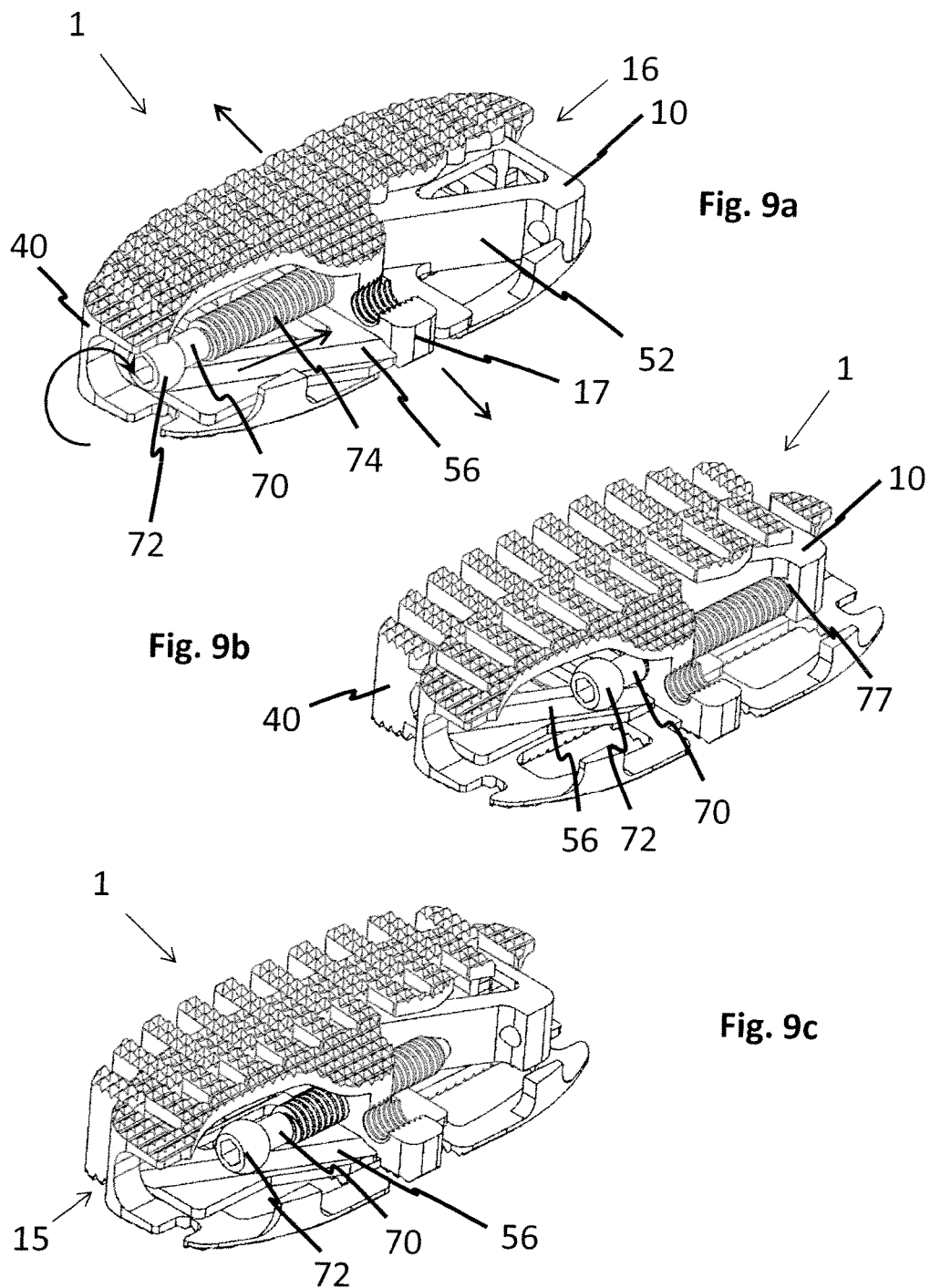

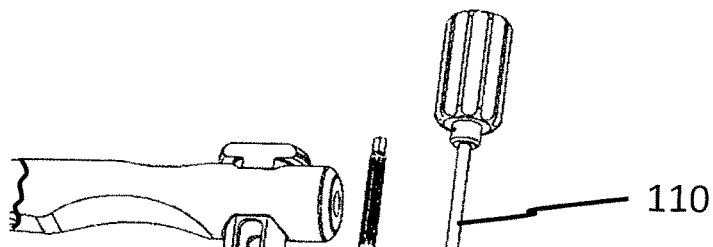
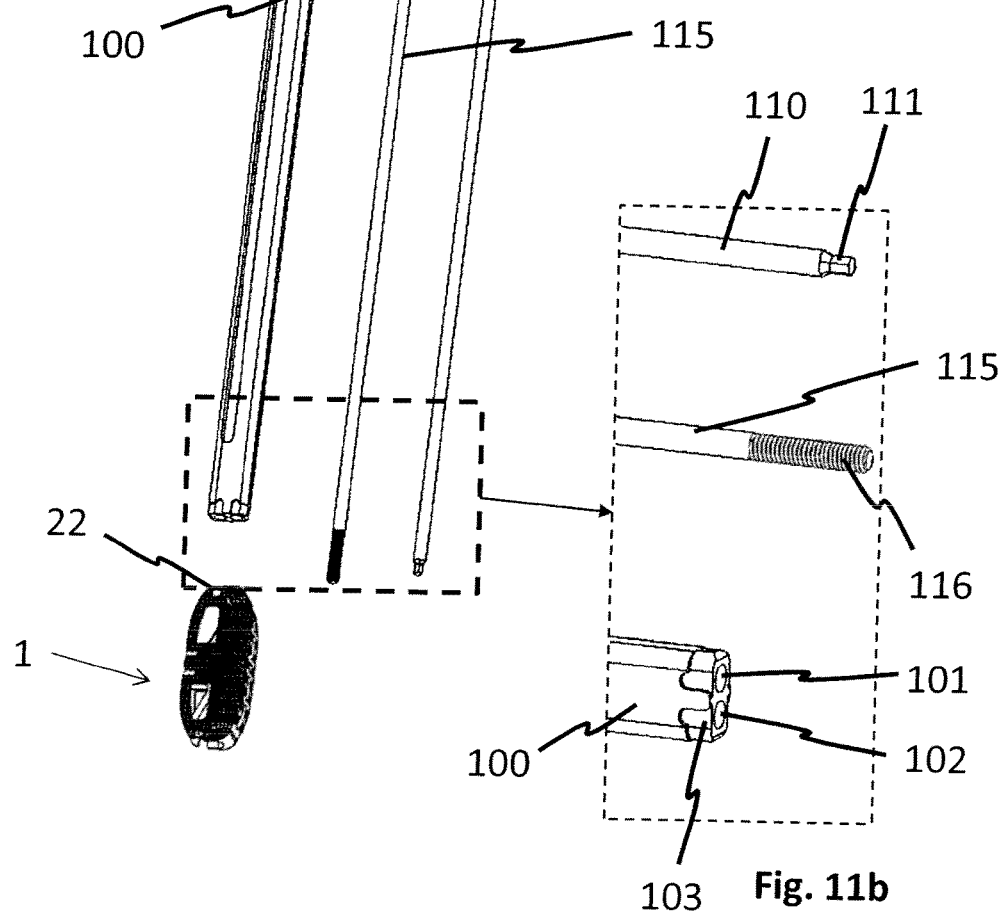
Fig. 11a
Fig. 11b

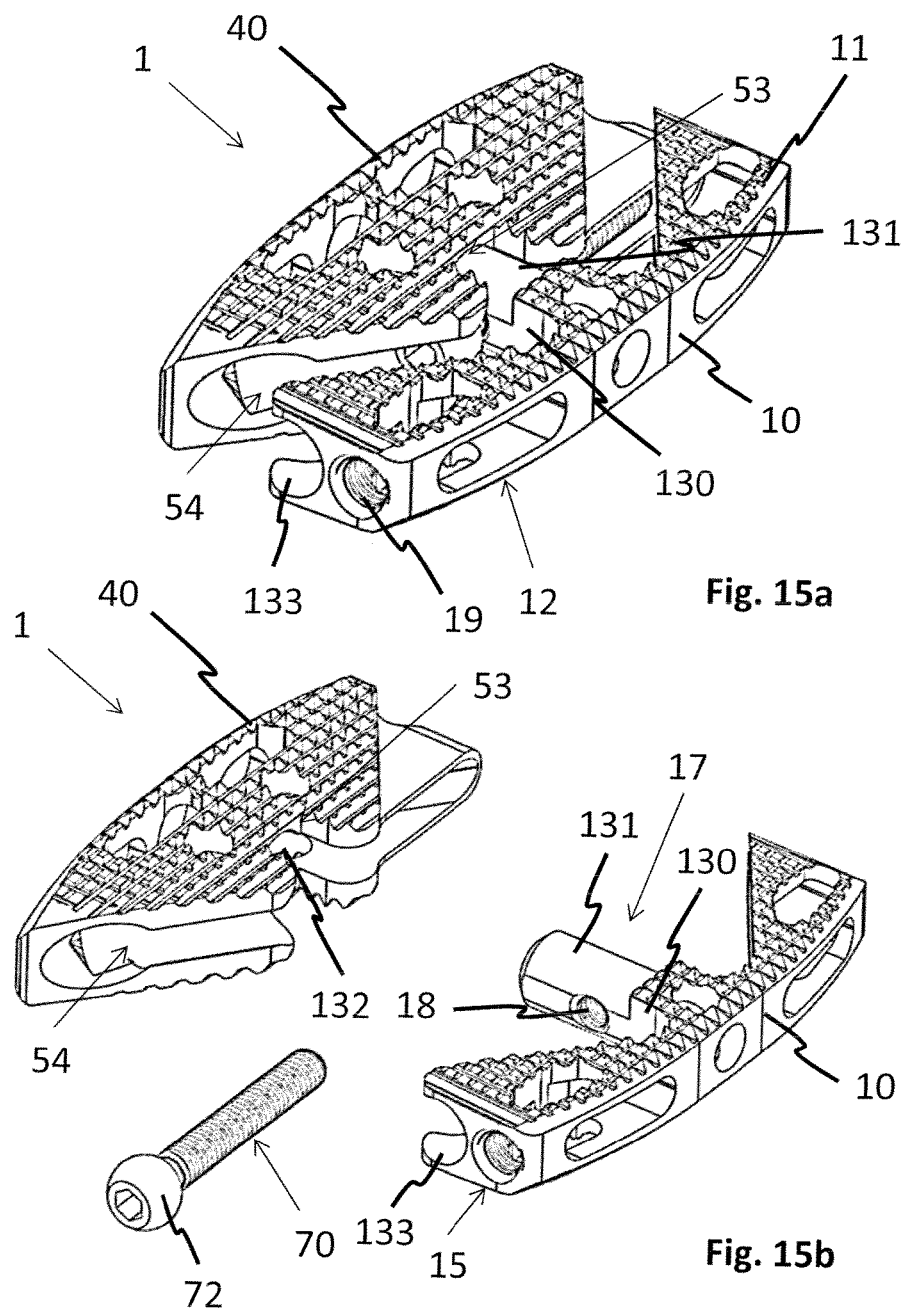

EXPANDABLE SPINAL IMPLANT

TECHNICAL FIELD

The invention relates to an expandable spinal implant assembly.

BACKGROUND ART

Low back pain is a common disease which may be caused by herniated discs, compressed nerve roots, degenerative discs or joint disease.

If a patient suffers severe low back pain and does not respond to conservative treatment, spinal fusion is an option to eliminate the pain. Spinal fusion is a surgical technique wherein two or more vertebrae are joined together. Spinal fusion interventions are also performed to correct back deformities.

With spinal fusion, often an intervertebral spacer or device is placed between the involved vertebrae after removal of the intervertebral disc. The intervertebral device corrects the spine alignment and restores the disc height.

Common intervertebral devices are made from titanium alloys or PEEK (polyetheretherketone) polymer. Often these devices comprise pockets that can be filled with bone graft material or artificial graft substitute. The fusion itself takes place when the bone of the vertebral endplates grows into and through the intervertebral device. Finally both vertebrae are grown together. Often, a pedicle system provides additional posterior stabilisation. Intervertebral fusion devices can be implanted with various approaches, for example with an anterior, posterior or lateral approach.

Over the past years minimally invasive techniques have been introduced. One advantage of the minimal invasive techniques is a reduction of soft tissue trauma resulting in a faster recovery. Other complications are reduced as well. In minimally invasive techniques the implant is brought into position between the vertebral bodies through a small incision with small instruments. However, the intervertebral device must still have a sufficient large foot-print to withstand the forces between the vertebrae before complete fusion has taken place. If a device has a too small foot-print it will sink into or break through an endplate of a vertebra, and the initially restored height is lost.

Combining advantages of the minimally invasive surgery approaches with intervertebral devices with large footprint affording a good support would require a device which may be brought into place through a small incision and which in a second step may be expanded to a larger size.

SUMMARY OF THE INVENTION

It is the object of the invention to create an expandable spinal implant assembly which may be implanted in a first, collapsed configuration with small dimensions and which may be transformed into a second, expanded configuration with a larger footprint by simple means. Further, the expandable spinal implant assembly should be easily collapsible in the event that the expandable spinal assembly has to be removed.

The solution of the invention is specified by the features of claim 1. According to the invention the expandable spinal implant assembly for insertion between two adjacent vertebral bodies comprises a substantially hollow first body with a first superior endplate having a first top inside face. The hollow first body further comprises a first inferior endplate with a first bottom inside face. Said first superior endplate and said first inferior endplate are connected together on at least one side by a lateral wall. At least one strut is arranged within said substantially hollow first body and connects the first top inside face of said superior endplate with the first bottom inside face of said inferior endplate. The strut comprises a first threaded through bore with a central axis. A central screw with a first end comprising a ball-head and a drive as well as having a threaded shaft is engaged within said first threaded through bore.

The expandable spinal assembly further comprises a substantially hollow second body with a second superior endplate and with a second inferior endplate. The substantially hollow second body is at least partially inserted within said substantially hollow first body. At least one track is arranged on a second top inside face of the second superior endplate and/or on a second bottom inside face of said second inferior endplate. The at least one track is oriented at an acute angle relative to the central axis of said first threaded through bore when said second substantially hollow body is inserted into said first substantially hollow body. The ball-head of said central screw is engaged into said at least one track.

With the arrangement of the ball-head within the at least one track, the expandable spinal implant assembly may be moved from a first, collapsed configuration into a second, expanded configuration having a larger footprint than said first configuration. I.e. the simple rotation movement of the central screw is transformed into a translation movement of the second substantially hollow body relative to the first substantially hollow body. Hence, a very simple yet effective mechanism for the expansion of the spinal implant assembly is established.

Both said first body and said second body are "substantially hollow". In the present application, "substantially hollow" is understood as a body having a defined shape which comprises a void space between the superior endplate and the inferior endplate, wherein said void may comprise at least one element spanning between said superior endplate and said inferior endplate, e.g. in the form of the at least one strut. Said superior endplate and said inferior endplate are connected together by at least one wall on a side face of said first implant body or said second implant body. At least one side face of both said first substantially hollow body and said second substantially hollow body does not comprise a wall such as to allow access to the central screw from the outside of the expandable spinal implant.

The "endplates" of the first body are those faces of the expandable spinal implant assembly which are positioned to bear against the vertebral bodies once the expandable spinal implant assembly is implanted.

The "endplates" of the second body are those faces which will at least partially be arranged next to the inside faces of the endplates of the first body.

The expandable spinal assembly preferably has a generally rectangular shape. More preferably, said superior and said inferior endplates of both said hollow implant bodies are generally oval in shape, wherein the front face is preferably straight.

The expandable spinal assembly hence has six faces. The upper and the lower faces are those faces which will bear against the endplates of the upper and the lower vertebral bodies, respectively, once implanted. Further, the expandable spinal assembly has an anterior and a posterior face. The posterior face is on the side of the expandable spinal implant assembly which will face towards the spinous process of the vertebra once implanted. Consequently, the anterior face is the side which will be oriented towards the torso of a patient. Additionally, the expandable spinal assembly comprises a front face and a back face. The front face is located on the side of the implant which is oriented towards a surgeon during an implantation of the expandable spinal assembly via a lateral approach. The back face is located on the side of the implant which is opposite the front face.

The strut preferably only partially spans along one dimension of the first body within said void space between the first superior endplate and the first inferior endplate. Preferably, the strut is arranged to be essentially parallel to the front side of said expandable spinal implant assembly.

The drive of the central screw is intended to be engaged with a surgical instrument, such as a screw driver. Hence, the drive preferably is in the form of a slot, Philips drive, hex socket, Torx drive or the like. The drive hence serves to transmit torsional moment from a surgical instrument to the central screw such as to entail a rotational movement of the central screw.

The at least one track is oriented at an acute angle relative to the central axis of said first threaded through-bore. An "acute angle" as used in the present application is understood to be an angle of less than 90° but more than 0°. By providing a track having an acute angle relative to the central axis of the first threaded through bore, a translational movement of the central screw along said central axis is transformed in a translational movement of the substantially hollow second body relative to the substantially hollow first body by the engagement of the ball head of the central screw into said at least one track. Preferably, said first body and/or said second body comprise means to guide said translation in a direction which is perpendicular to said central axis of the first threaded through bore.

Preferably, said acute angle of said at least one track relative to said central axis of the first through bore is such that the at least one track is inclined in an anterior to posterior direction as seen from the front side. Hence, a translation of the central screw towards the rear side will result in an increase of the footprint of the expandable spinal implant assembly, as the second body is pushed out of the void between the endplates of the first body towards the expanded configuration.

Alternatively, the acute angle of said at least one track relative to said central axis of the first through bore is such that the at least one track is inclined in a posterior to anterior direction as seen from the front side. In this variant, the expansion of the expandable spinal implant assembly is achieved by a translation of the central screw towards the front side.

By varying the acute angle of the at least one track relative to the central axis of the first threaded through bore and/or the thread pitch of said first threaded through bore and said central screw, the translation speed of said second body relative to said first body may be varied.

Preferably, the expandable spinal assembly includes a superior track located on said second top inside face of said second superior endplate and an inferior track located on said second lower inside face of said second inferior endplate, said superior track and said inferior track being arranged symmetrically to each other and forming a cylindrical channel.

In this embodiment of the present invention, the ball head of the central screw is engaged in both said superior track and said inferior track. Preferably, said superior track and said inferior track have the same centre and radius, e.g. they both form an arc of the same cylindrical channel. This allows an easy manufacture of said superior and said inferior tracks, as they may be made using a drill. Preferably, the radius of said cylindrical channel is marginally larger than a maximal radius of the ball head.

Preferably, the acute angle of said at least one track relative to said central axis of the first threaded through bore is between 5° and 45°, more preferably between 10° and 30°. By using angles within said range, an optimal translational speed of said second body relative to said first body may be achieved.

Further, the force with which the expandable spinal implant assembly expands is related to the angulation of the acute angle. The lower the angle is, the larger the exerted force of the expandable spinal implant assembly will be.

The first body preferably comprises at least one slot and said second body preferably comprises at least one protrusion. The at least one protrusion is configured to engage with said at least one slot. Further, said protrusion substantially extends to said first superior endplate and to said first inferior endplate.

Hence, the at least one slot and at least one protrusion interact with each other in a zip like manner. As said at least one slot substantially extends to the first superior endplate and the first inferior endplate, i.e. said at least one slot is flush with said first endplates, the expandable spinal implant assembly provides a substantially flat support for the vertebral bodies of the two adjacent vertebrae both in said first, collapsed configuration and in said second, expanded configuration.

In a preferred embodiment, said first body and said second body each comprise a multitude of slots and protrusions, respectively. Most preferably, the number of protrusions matches the number of slots.

Preferably, the strut comprises a second threaded through bore adjacent said first threaded through bore for engagement with a coupling core of an insertion instrument. This allows to couple said expandable spinal implant assembly with an insertion instrument by means of e.g. a threaded coupling core.

Preferably, a first front side of said first implant body comprises a recess in said first superior endplate and said first inferior endplate. Said recess is preferably arranged parallel to a second central axis of said second through bore for forming a connection means with the insertion instrument.

By providing said recess, the expandable spinal implant assembly may be connected with the insertion instrument in an angle stable manner, i.e. any rotation of the expandable spinal implant assembly around an axis of the insertion instrument is prevented by the engagement of the insertion instrument with said recess.

The first top inside face and the first bottom inside face are preferably spaced from each other by a first distance D1 and are substantially parallel to each other. The second superior endplate and the second inferior endplate are arranged substantially parallel to each and are spaced from each other by a second distance D2 which is smaller than said first distance D1.

Hence, the second body has a height which is smaller than the distance between the first top inside face and the first bottom inside face of the first body. This allows the second body to be at least partially inserted into the first body. Preferably, the difference between the first distance D1 and the second distance D2 is selected such that the second superior endplate and the second inferior endplate engage with the first top inside face and the first bottom inside face, respectively, while allowing a gliding motion of the endplates relative to the inside faces. For example, the first distance D1 may be 0.2 mm bigger than the second distance D2.

The ball head of said central screw is preferably a cylindrical head, a conical head or a double conical head. These shapes of the ball head provide a good interaction with the at least one track, especially in cases where the at least one track is provided in the form of an arc of a cylindrical channel.

The second body preferably comprises at least one second track arranged on a second top inside face of said second superior endplate and/or on a second bottom inside face of said second inferior endplate, said at least one second track being oriented parallel relative to the central axis of said first through bore.

Preferably, said at least one second track is arranged such as to be co-axial with the central axis of the first threaded though bore when said expandable spinal implant assembly is in the first, collapsed configuration. Hence, the central screw may be easily inserted and removed when the expandable spinal implant assembly is in the first, collapsed configuration.

The strut preferably comprises a first portion connecting the first top inside face of the superior endplate with the first bottom inside face of the inferior endplate and a second cylindrical portion extending therefrom. The second body preferably comprises a guiding bore for receiving said second cylindrical portion.

This allows a further guiding of a translation of the first body relative to the second body when said expandable spinal implant assembly is moved from the first, unexpanded configuration to the second, expanded configuration or vice versa.

In this embodiment, the first threaded through bore is preferably located on said second cylindrical portion.

Said ball head of said central screw has a second diameter and said elongated shaft of said central screw has a third diameter, wherein the ratio between said second diameter and said third diameter preferably is at least 110:100, more preferably at least 130:100.

The expandable spinal implant assembly has a first footprint in the first, unexpanded configuration and a second footprint in the second, expanded configuration, wherein the ratio between said first footprint and said second footprint preferably is at least 100:125.

In the present application, the term "footprint" is understood as the area of a vertebra covered by said expandable spinal implant assembly, i.e. an area which corresponds to the product of the first length L1 and the first width W1 or the second width W2, respectively.

Hence, in this preferred embodiment, the footprint in said second, expanded configuration is at least 25% larger than in said first, unexpanded configuration. It is to be noted that said increase in footprint is mediated uniquely by an increase of the width of the expandable spinal implant assembly, while the first length L1 does not vary between said first, unexpanded configuration and said second, expanded configuration.

Said spinal implant assembly has a first length L1 and said central screw (70) has a third length L3, wherein the ratio between said first length L1 and said third length L3 is smaller than 100:80, preferably smaller than 100:70.

With this ratio, it may be ensured that the central screw will not protrude from the expandable spinal implant assembly in the second, expanded configuration, while the third length L3 is sufficient to provide enough translational movement of the central screw within said first threaded through bore and hence of the ball head within said at least one track to ensure an efficient expansion of the expandable spinal implant assembly from the first, unexpanded configuration to the second, expanded configuration.

Preferably, said first element, said second element and said central screw are made of titanium, a titanium allow, stainless steel or a biocompatible polymer, preferably polyetheretherketone (PEEK).

A further aspect of the present application is to provide a kit comprising at least two expandable spinal implant assemblies according to the present invention. The at least two expandable spinal implant assemblies differ in at least one of the following: the first length L1, a first width W1 in the unexpanded configuration, a second with W2 in the expanded configuration, the first distance D1, the second distance D2, a first inclination angle and/or a second inclination angle of said first upper endplate relative to said first lower endplate or of said second upper endplate relative to said second lower endplate, respectively.

Such a kit allows a surgeon to choose the best fitting expandable spinal implant assembly for a patient.

A further aspect of the present application is to provide a method for spinal fusion using an expandable spinal implant assembly according to the present invention. Said method comprises as a first step the removal of an intervertebral disc between two adjacent vertebrae. Various methods on how to remove a vertebral disc are known to a person having skill in the art. In a second step, an expandable spinal implant assembly according to the present invention is placed between said two adjacent vertebrae in the first, collapsed configuration. Said first, collapsed configuration has a first footprint. Afterwards, the expandable spinal implant assembly is expanded to the second, expanded configuration by rotation of the central screw, e.g. by means of a screw driver or power tool. The second, expanded configuration has a second footprint which is larger than said first footprint.

Preferably, the placement of said expandable spinal implant assembly is performed using an insertion instrument which is coupled to said expandable spinal implant assembly by means of a threaded tip of a coupling core of said insertion instrument threadably engaged with a second through bore of said expandable spinal implant assembly.

Other advantageous embodiments and combinations of features come out from the detailed description below and the totality of the claims.

BRIEF DESCRIPTION OF THE DRAWINGS

The drawings used to explain the embodiments show:

FIGS. 3a, 3b different perspective views of the second body according to the first embodiment;

FIGS. 9a-9c the interaction of all individual components of the expandable implant assembly according to the second embodiment in perspective views;

FIGS. 11a, 11b an insertion instrument used in connection with an expandable spinal implant assembly according to the present invention;

FIGS. 15a, 15b a further embodiment of the expandable spinal implant assembly.

In the figures, the same components are given the same reference symbols.

PREFERRED EMBODIMENTS

Figure 1A:
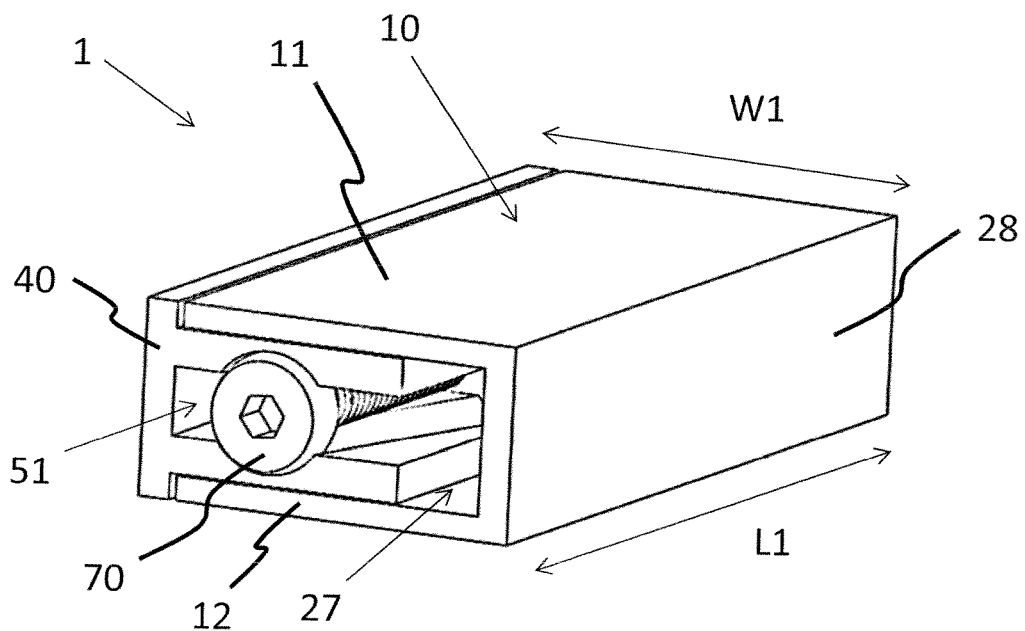
FIGS. 1a, 1b a perspective representation of a first embodiment of an expandable spinal implant assembly according to the present invention.
Figure 1B:
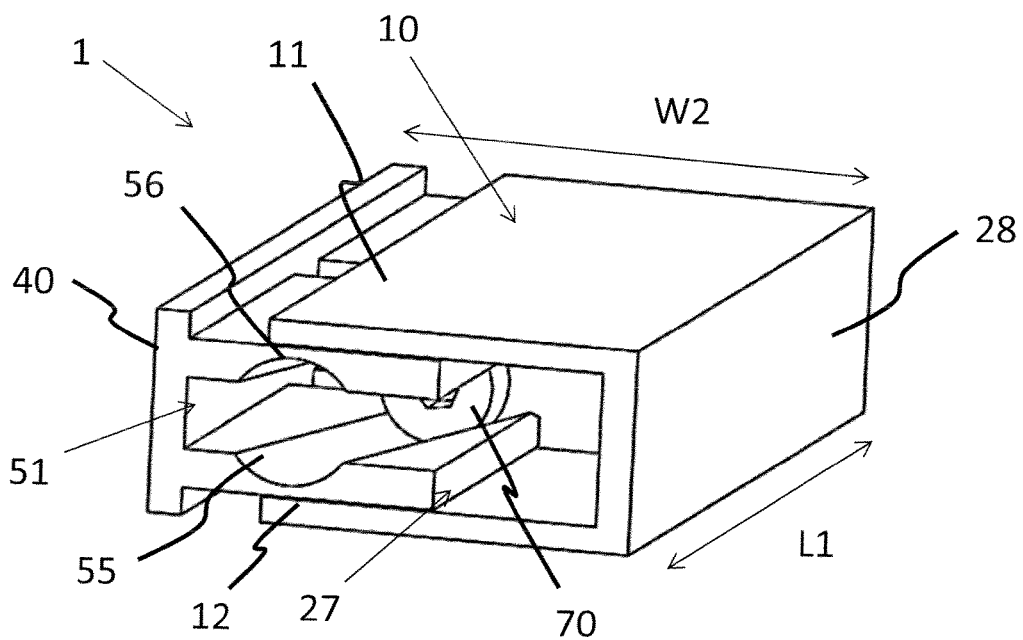

FIGS. 1a and 1b show a perspective representation of a first embodiment of an expandable spinal implant assembly 1. In FIG. 1a, the expandable spinal implant assembly 1 is in a first, collapsed configuration. In this configuration the expandable spinal implant assembly 1 has a first footprint surface area defined by a first width W1 and a first length L1.

FIG. 1b shows the expandable spinal implant assembly 1 in a second, expanded configuration. In said second configuration, the expandable spinal implant assembly 1 has a second footprint surface area defined by a second width W2 and the first length L1. The second width W2 is larger than said first width W1.

The expandable spinal implant assembly comprises a substantially hollow first body 10. The first body 10 includes a first superior endplate 11 and a first inferior endplate 12. Said first endplates 11, 12 are connected together by a first side plate 28. Between said two first endplates 11, 12 and said first side plate 28 the substantially hollow first body 10 comprises a first void 27.

Further, the expandable spinal implant assembly 10 comprises a substantially hollow second body 40. Said second body 40 includes a second superior endplate 41 and a second inferior endplate 42. Both said second endplates 41, 42 are connected together by a second side plate 48. Between said two second endplates 41, 42 and said second side plate 48 the substantially hollow second body 40 comprises a second void 51.

The expansion of the expandable spinal implant assembly 1 is caused by a translation of the first body 10 relative to the second body 40. This translation results in an increase of the overall width of the expandable spinal implant assembly 1 from the first width W1 to the second width W2.

Translation of the two bodies 10, 40 relative to each other is caused by a translation of a central screw 70 in a direction which is substantially perpendicular to the translation direction of the second body relative to the first body. A ball head 71 of said central screw 70 is engaged in a cylindrical channel defined by two tracks 55, 56 arranged opposite each other on the inside of said second body 40 and being configured to have an acute angle relative to said central screw 70. When said central screw 70 is rotated a threaded engagement of said central screw 70 will cause a translation of the central screw 70 along said two tracks 55, 56. As the two tracks 55, 56 include an acute angle in relation to the central screw 70, the translation of the central screw 70 within the two cylindrical channels 55, 56 will cause a translational movement of said substantially hollow second body 40 relative to said substantially hollow first body 10.

Figure 2A:
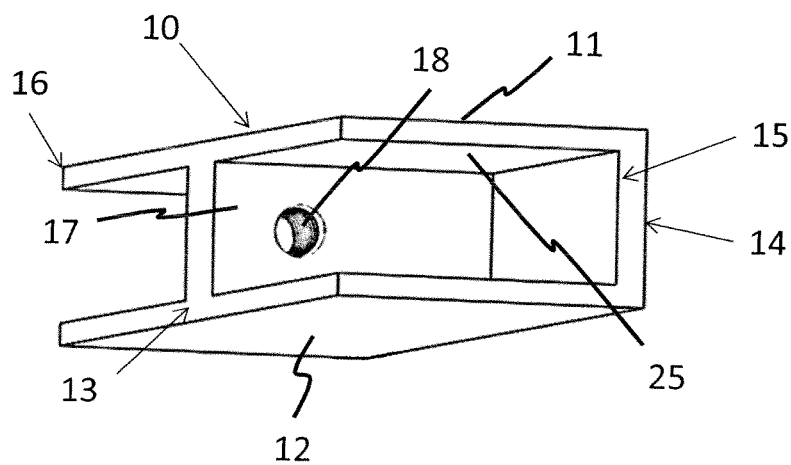
FIGS. 2a, 2b different perspective views of the first body according to the first embodiment.
Figure 2B:
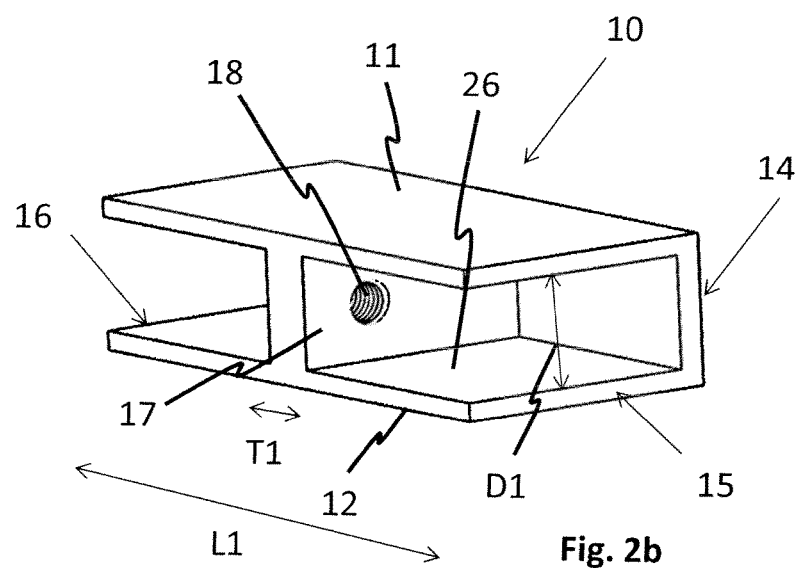

FIGS. 2a and 2b show different perspective views of said first body 10. The first body 10 comprises a first superior endplate 11 and a first inferior endplate 12. The first body 10 has a first anterior end 13, a first posterior end 14, a first front side 15 and a first rear side 16. The first superior endplate 11 and the first inferior endplate 12 define a first inner top face 25 and a first inner bottom face 26, respectively. A strut 17 is arranged between said first inner top face 25 and said first inner bottom face 26, spanning from said first posterior end 14 to said first anterior end 13. The strut has a first thickness T1 which is oriented in the direction from the first front side 15 to the first rear side 16. The ratio between the first thickness T1 and the first length L1 of the expandable implant assembly 1, which corresponds to the length of the first body 10, is preferably larger than 1:3, preferably between 1:7 and 1:15.

The first superior end plate 11 and the first inferior endplate 12 are connected by the strut 17 and by the first side plate 28, which spans between said first endplates 11, 12 along said posterior end 14 of the substantially hollow first body 10.

The strut 17 is located substantially centrally between said first front side 15 and said first rear side 16. The strut 17 comprises a first threaded through bore 18. The first threaded through bore 18 is intended for engagement with said central screw 70.

FIGS. 3a and 3b show the second body 40 in different perspective views. The second body 40 comprises a second superior endplate 41 and a second inferior endplate 42 located at a second top side 48 and a second bottom side 49, respectively. Further, the second body 40 has a second anterior end 43, a second posterior end 44, a second front side 45 and a second rear side 46. The second superior endplate 41 and the second inferior endplate 42 are parallel to each other and include a second void 51 between each other. The second superior endplate 41 and the second inferior endplate 42 are spaced from each other by a second distance D2.

The second endplates 41, 42 are joined together at the second anterior end 43 by a second side plate 59. The second side plate 59 is dimensioned such as to extend over the second superior endplate 41 and the second inferior endplate 42, such as to form two protrusions 47.1, 47.2 on said second top side 48 and said second bottom side 49. Said protrusions 47.1, 47.2 are dimensioned to substantially extend to the level of the first superior endplate 11 and the first inferior endplate 12, respectively, of the first body 10 when said second body 40 is at least partially inserted into said first body 10.

The second superior endplate 41 and the second inferior endplate 42 comprise a guiding recess 53 extending from the second posterior end 44 to the second side plate 59. Said guiding recess 53 has a third width W3, wherein said third width W3 is substantially equal to the first thickness T1 of the strut 17 of the first implant body 10.

Further, a cylindrical channel 54 with a first diameter A1 is defined by a superior track 55 located on a surface of a second top inside face 57 of the second superior endplate 41 facing towards the second void 51 and by an inferior track 56 located on a surface of a second bottom inside face 58 of the second inferior endplate 42 facing towards the second void 51. The tracks 55, 56 extend from said second front side 45 towards said guiding recess 53. The tracks 55, 56 form an acute angle with the second front side 54. Once the second body 40 is at least partially inserted into the first body, the tracks 55, 56 will include an acute angle relative to the axis of the first trough bore 18.

Figure 4:
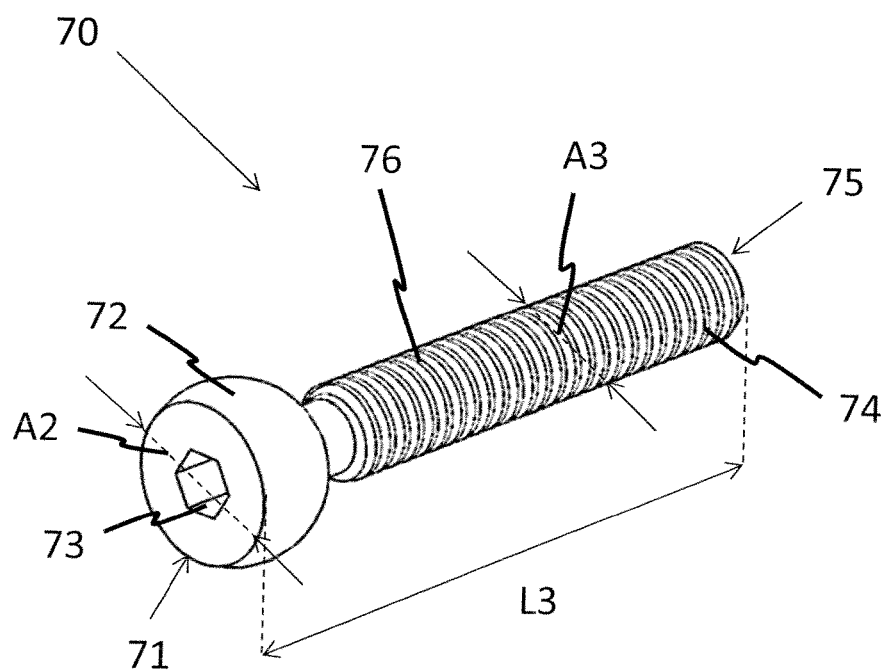
FIG. 4 a detailed representation of the central screw.

FIG. 4 shows the central screw 70 in greater detail. The central screw 70 has a first end 71 with a ball-head 72. The ball-head 72 includes a drive 73 and has a second diameter A2. The second diameter A2 is substantially equal to the first diameter A1 of the cylindrical channel 54 of the second body 40. The central screw 70 furthermore comprises an elongated shaft 74 extending from said first end 71 to a second end 75. The elongated shaft 74 is a threaded shaft having an outer screw thread 76 and a third diameter A3. The central screw 70 has a third length L3. The third length L3 spans the entire elongated shaft 74 as well as the ball-head 72. In a preferred embodiment, the ratio between the second diameter A2 and the third diameter A3 is larger than 110:100, preferably larger than 130:100. With a large ratio between the second diameter A2 and the third diameter A3 the transfer of translational forces between the central screw 70 and the cylindrical channel 54 is enhanced.

Preferably, the ratio between the first length L1 of the expandable spinal implant assembly 1 and the third length L3 of the central screw 70 is smaller than 100:80, preferably smaller than 100:70.

Figure 5A:
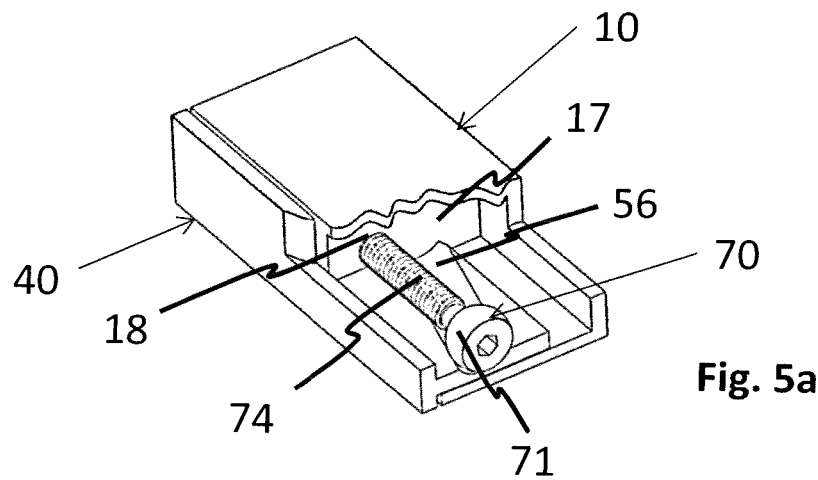
FIGS. 5a-5c the interaction of all individual components of the expandable implant assembly according to the first embodiment in perspective views.
Figure 5B:
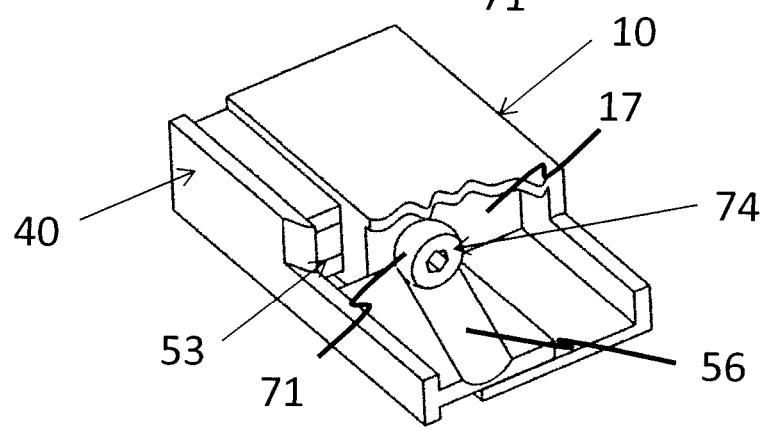
Figure 5C:
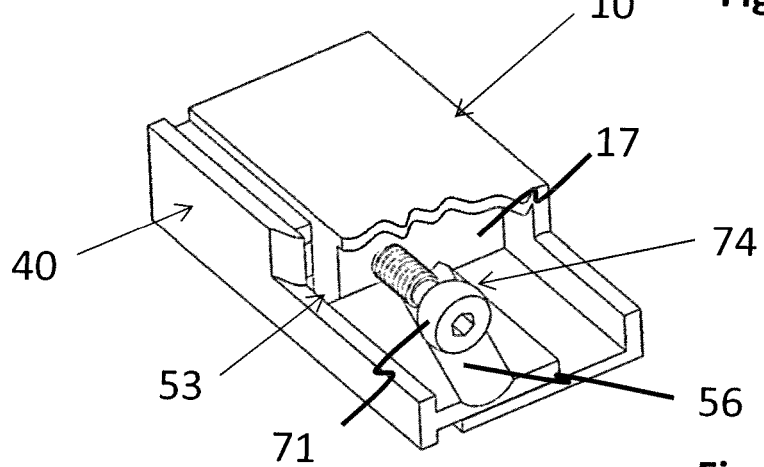

FIGS. 5a to 5c show the interaction of all individual components of the expandable implant assembly 1 in perspective views. The first body 10 and the second body 40 are shown in a partial cross-sectional view.

FIG. 5a depicts the expandable implant assembly 1 in a first, collapsed configuration. The elongated shaft 74 of the central screw 70 is engaged into first threaded through bore 18 of the strut 17 of the first body 10. Simultaneously, the ball-head 72 of the central screw 70 is engaged within the superior track 55 and the inferior track 56 of the second body 40. The strut 17 is arranged within the guiding recess 53. This restricts the movement of the bodies 10, 40 relative to each other to the direction of the recess 53 and prevents any motion of the bodies 10, 40 relative to each other in any other direction. Further, the interaction of said first top inside face 25 with the second superior endplate 41 and the interaction of the first bottom inside face 26 with the second inferior endplate 42 prevents any vertical or angular motion of the two bodies 10, 40 relative to each other.

FIG. 5b shows the expandable implant assembly 1 in a second, expanded configuration. Upon rotation of the central screw 70, e.g. by means of an instrument coupled to the drive 73, a linear motion will be imparted on said central screw 70 by the interaction of the outer thread 76 on the elongated shaft 74 with the first threaded through bore 18. The engagement of the ball head 72 within the tracks 55, 56 leads to a transfer of this motion onto the second body 40. As the tracks 55, 56 form an angle with the second front side 54 as well as with the axis of the first through bore 18 and the second body 40 is blocked of moving in the translational direction of the central screw 70 relative to the first body 10 by the engagement of the guiding recess 53 with said strut 17, the linear motion of the ball head 72 within the first threaded through bore 18 is transformed into a translational motion of the substantially hollow bodies 10, 40 relative to each other in a direction which is perpendicular to the axis of said through bore 18 by the engagement of the ball head 72 within said tracks 55, 56. As a result, by rotating the central screw 70 the second body 40 is pushed relative to the first body 10 towards the second, expanded configuration.

Often in surgery an implant must be removed. Therefore any implant that can expand must be collapsible as well. FIG. 5c shows the collapsing of the expandable spinal implant assembly 1 from the second, expanded configuration towards the first, collapsed configuration. Upon unscrewing of the central screw 70, the ball head 72 is moved towards the first front side 15 of the first implant body 10. The ball-head 72 located in the tracks 56, 57 will exert a force upon said substantially second hollow body pulling said second body 40 back into the first void 27 of said first body 10.

FIGS. 6a to 6d show different perspective views of a first body 10 according to a second embodiment of the expandable spinal implant assembly 1.

The first superior endplate 11 and the first inferior endplate 12 are arranged relative to each other under a first inclination angle 29. The first inclination angle 29 is chosen such as to match the lordotic curve of the natural spine. The inclination angle may thus vary from 3° to 20°, preferably from 8° to 10°.

In reference to the first superior endplate 11 and the first inferior endplate 12 at the first anterior end 13, the first endplates 11, 12 each comprise multiple slots 20a-20z, extending through the endplate in an anterior to posterior direction. These slots 20a-20z define fingers 21a-21z. In a preferred embodiment the first body 10 comprises at least three fingers 21a-21z, defined by at least two slots 20a-20z. In essence, there is always one slot 20a-20z less than the number of fingers 21a-21z. A second length L2 of the slots 20a-20z in anterior to posterior direction is at least equal to the difference between the second width W2 of the expandable spinal implant assembly 1 in the expanded configuration and the first width W1 of the expandable spinal implant assembly 1 in the collapsed configuration.

Figure 6A:
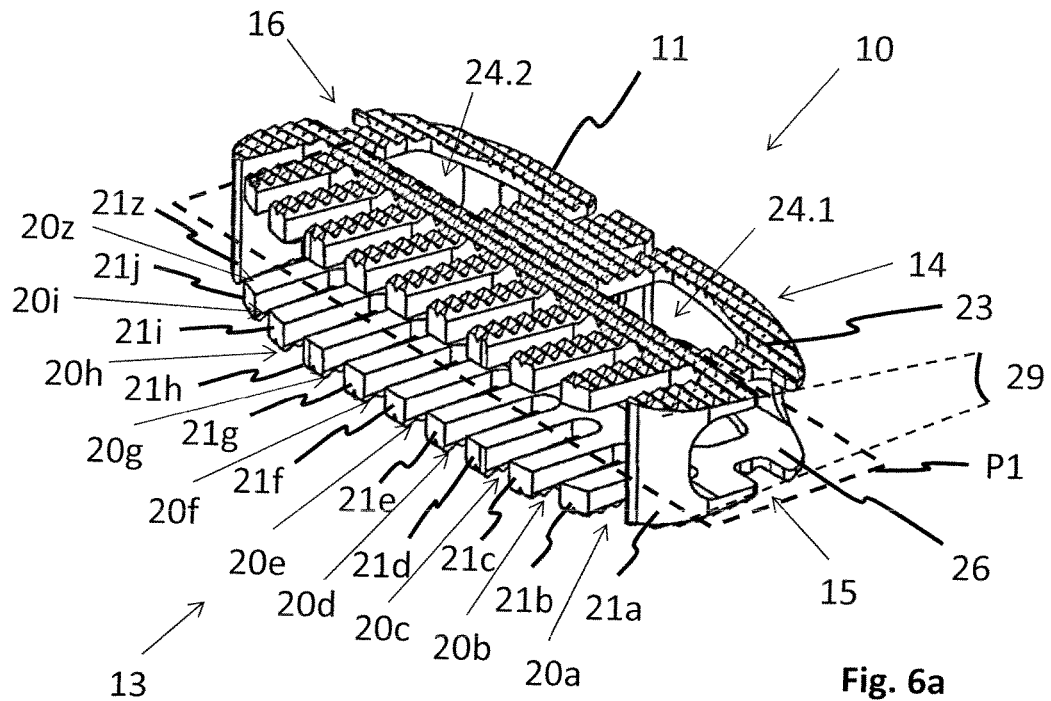
FIGS. 6a-6d different perspective views of the first body according to a second embodiment of the expandable spinal implant assembly.
Figure 6B:
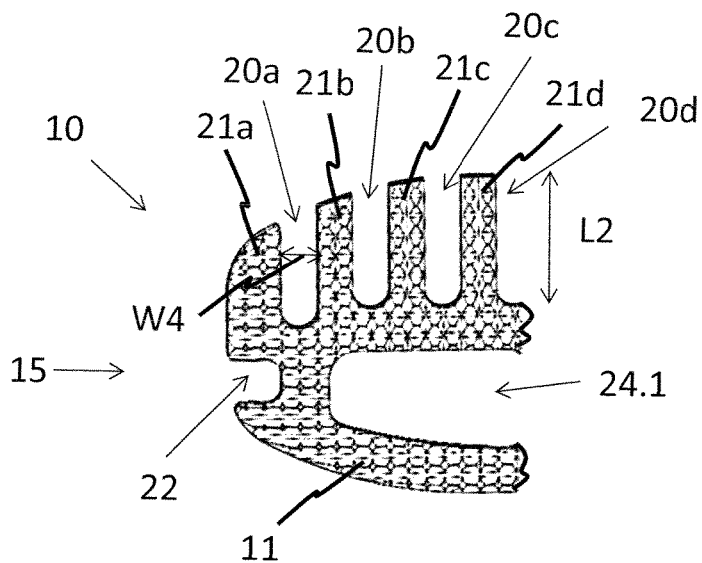

FIG. 6b is a top view of the first body 10 where the dimensions and the arrangement of the slots 20a-20z is more clearly visible. As depicted in this figure, the slots 20a-20z are defined by a second length L2 and a fourth width W4. Further, the first body 10 comprises one recess 22 in both said first endplates 11, 12. Said recess 22 is intended for engagement with an insertion instrument. In a preferred embodiment, the first body 10 is symmetrically configured in relation to central plane 'P1'. Due to this symmetry, the first body 10 may be used in two orientations, i.e. the first top endplate 11 and the first inferior endplate 12 may be flipped.

The first endplates 11, 12 comprise teeth 23 or another rough structure for primary fixation over friction with the vertebral bodies once implanted. Further, one or more pockets 24.1, 24.2 are provided in each of said first endplates 11, 12 to allow for bone-graft placement and bone in-growth. The pockets 24.1, 24.2 connect the first void 51 with the space adjacent said first endplates 11, 12.

Figure 6C:
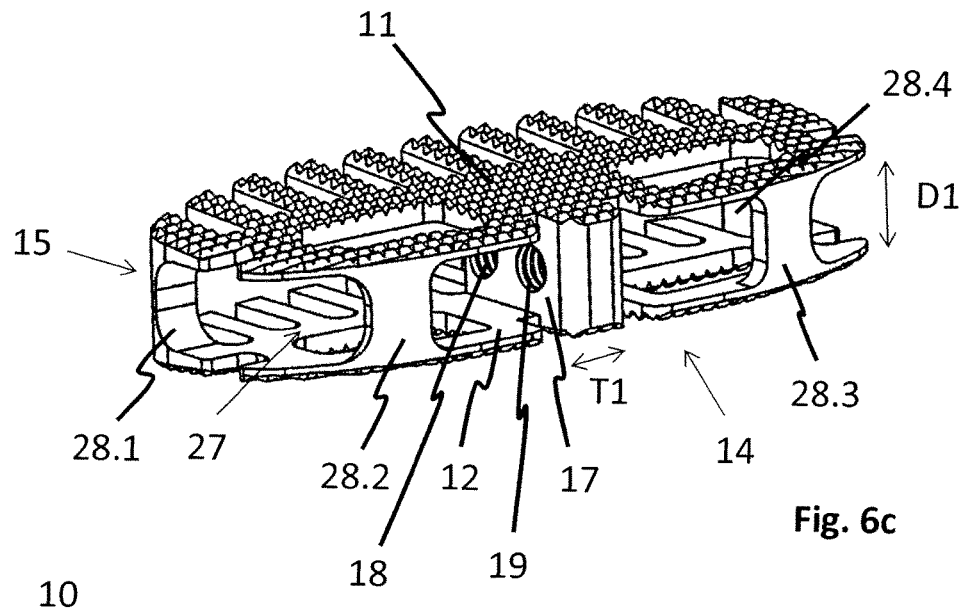
Figure 6D:
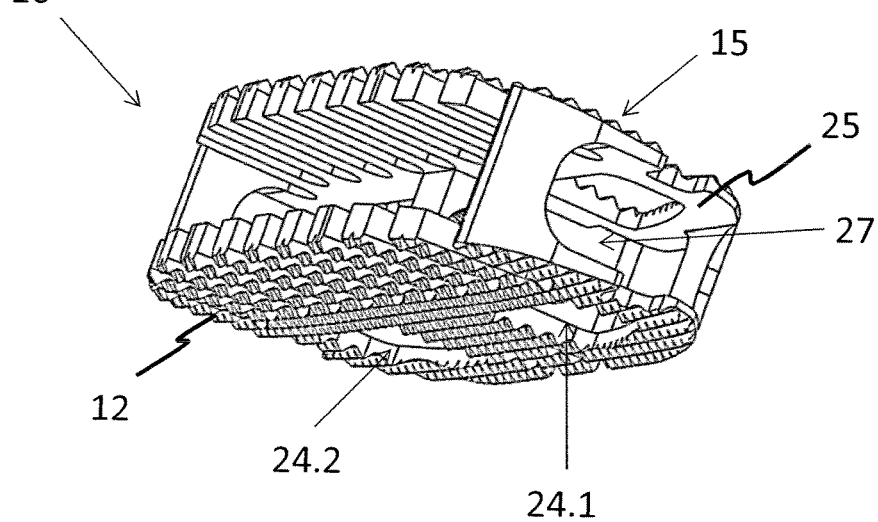

FIG. 6c show the substantially hollow first body 10 according to the second embodiment of the expandable spinal implant assembly 1 from the first posterior end 14. In contrast to the first embodiment as shown in FIGS. 1 to 5, the first side plate 28 is replaced by four support struts 28.1, 28.2, 28.3, 28.4. Each support strut 28.1, 28.2, 28.3, 28.4 transfers loads exerted on the first superior endplate 11 to the first inferior endplate 12 and vice versa. In a preferred embodiment, the first body 10 comprises four support struts 28.1, 28.2, 28.3, 28.4 which are substantially evenly divided along the posterior end 14. Alternatively, the first body 10 may comprise either more or less support struts 28.1, 28.2, 28.3, 28.4. The position, shape and size of the support struts 28.1, 28.2, 28.3, 28.4 may also vary. The support struts 28.1, 28.2, 28.3, 28.4 are configured for an optimal load transfer, but are preferably as small as possible to provide as much space as possible for bone in and over-growth, which finally causes the spinal vertebral bodies to fuse. The position, shape and size of the support struts 28.1, 28.2, 28.3, 28.4 may also vary depending on the chosen manufacturing technique, such as for example milling, wire EDM for titanium implants, or milling and injection moulding for PEEK implants.

The ratio between the first thickness T1 of the strut and the first length L1 of the expandable spinal implant assembly 1 preferably is larger than 1:3 and more preferably lies in a range of between 1:7 and 1:15. The strut 17 is located substantially centrally between said first front side 15 and said first rear side 16. In addition to the first threaded through bore 18, the strut 17 comprises a second threaded through bore 19. The first threaded through bore is intended for engagement with the central screw 70, while the second threaded through bore 19 is intended for engagement and coupling with an insertion instrument.

Figure 7A:
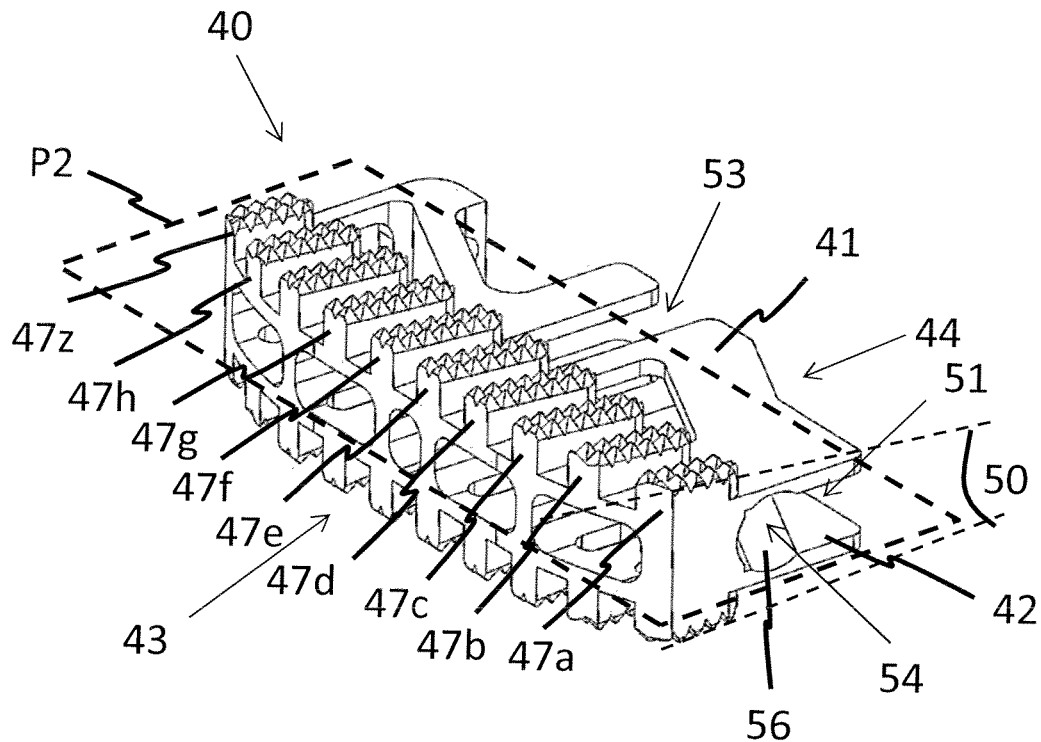
FIGS. 7a-7c different perspective views of the second body according to the second embodiment of the present invention.
Figure 7B:
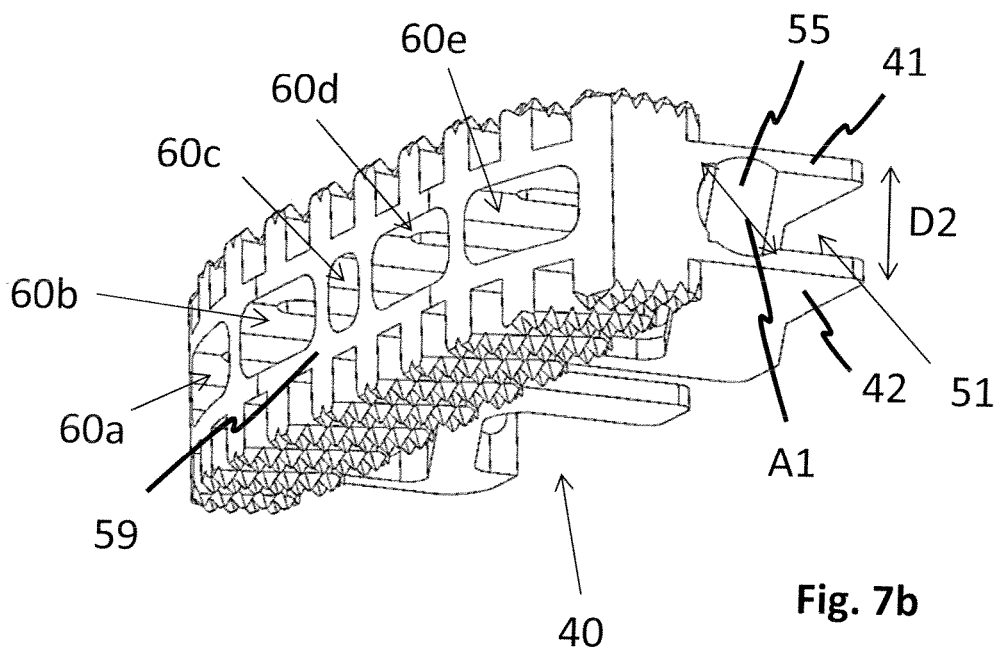
Figure 7C:
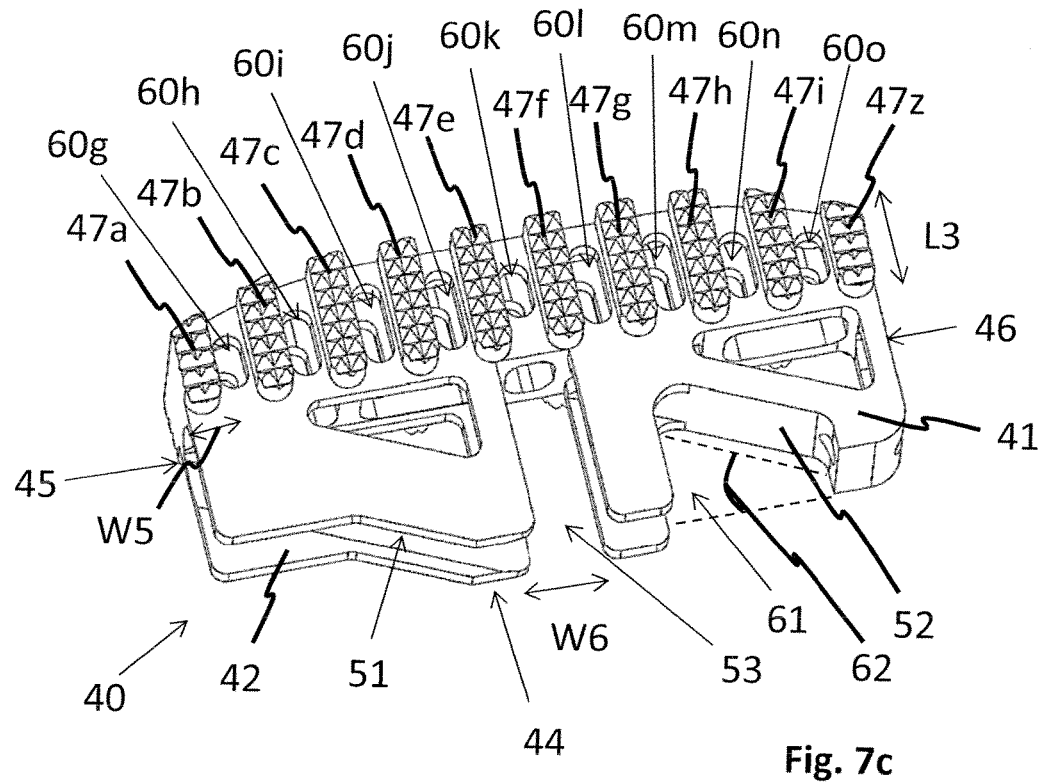

FIGS. 7a to 7c show different perspective views of the substantially hollow second body 40 according to the second embodiment of the present invention. The second superior endplate 41 and the second inferior endplate 42 are substantially parallel and spaced to each other by the second distance D2. At the second anterior end 43, multiple elongated protrusions 47a-47z extend from said second superior endplate 41 and said second inferior endplate 42. Each protrusion 47a-47z has a third length L3 and fifth width W5, wherein the third length L3 and the fifth width W5 are substantially equal to the dimensions of the slots 20a-20z of said first body 10, which are defined by the fourth width W4 and the second length L2. The protrusions 47a-47z form the second top side 48 and the second bottom side 49 and extend to the level of the first superior endplate 11 and the first inferior endplate 12 of the first body 10. The second top side 48 and the second bottom side 49 may be oriented under a second inclination angle 50 relative to each other. The second inclination angle 50 is chosen to match the lordotic curve of the natural spine. The second inclination angle 50 may vary from 3° to 20°, preferably from 8° to 10°. The second inclination angle 50 is equal to the first inclination angle 29 of the substantially hollow first body 10.

The protrusions 47a-47z comprise teeth or another rough structure for primary fixation over friction with the vertebral bodies.

FIG. 7c shows a detailed view of the second body 40 from the second posterior end 44. The second void 51 comprises angled slope 52. The angled slope 52 is arranged in a posterior recess 61 which spans from said second superior endplate 41 to said second inferior endplate 42. The angled slope 52 is arranged at a third inclination angle 62 relative to the second posterior end 44.

The guiding recess 53 extends from the second superior endplate 41 to the second inferior endplate 42 and has a sixth width W6, wherein said sixth with W6 is substantially equal to the first thickness T1 of the strut 17 of the first body 10.

The cylindrical channel 54 has the first diameter A1 and extends from the second front side 45 towards the guiding recess 53. As for the first embodiment, the cylindrical channel 54 of the second embodiment is defined by the superior track 55 and the inferior track 56. The superior track 55 and the inferior track 56 are circular in shape and share the identical centre and radius. Alternatively at least one of the tracks 55, 56 may have a quadratic or triangular shape.

The second body 40 is symmetrically configured in relation to a second central plane P2. Due to this symmetry the second body 40 may be used in two orientations, i.e. flipped in relation to the second central plane P2.

The second body 40 comprises multiple pockets 60a-60z for bone-graft placement and bone in-growth. Said pockets 60a-60z are located at the second anterior end 43 as well as the second superior endplate 41 and the second inferior endplate 42. The pockets 60a-60z at least partially connect the second void 51 with the outside of the expandable spinal assembly 1.

Figure 8A:
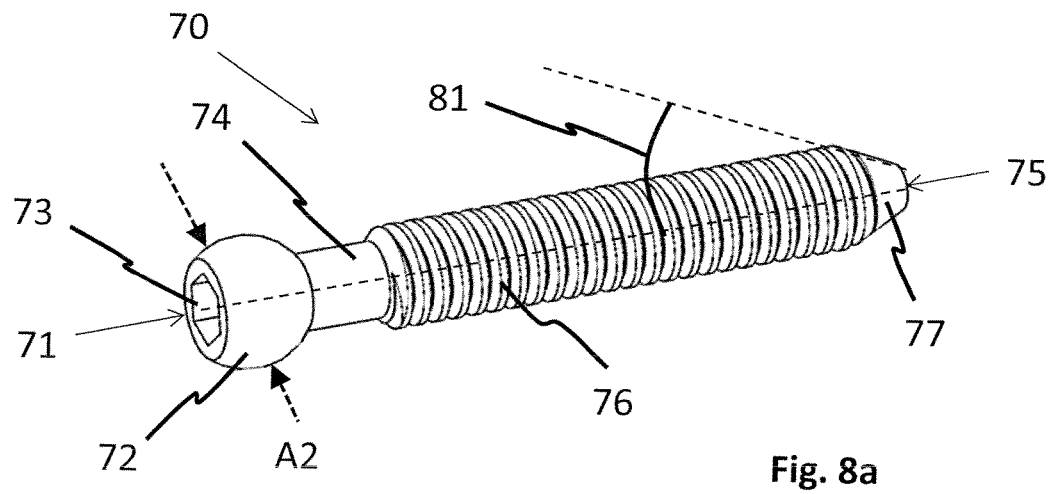
FIGS. 8a-8d different embodiments of the central screw.

FIG. 8a shows the central screw 70 in greater detail. The central screw 70 comprises a first end 71 with a ball-head 72. The ball-head 72 includes a drive 73. Said ball-head 72 has a second diameter A2 which is substantially equal to the first diameter A1 of the cylindrical channel 54 of the second body 40. The central screw 70 furthermore comprises an elongated shaft 74 extending from said first end 71 to a second end 75. The elongated shaft 74 is a threaded shaft having an outer screw thread 76 extending from said ball-head 72 to said second end 75. In an alternative embodiment the said outer screw thread 76 is a screw thread with a double or triple lead to facilitate a larger translation per turn. The elongated shaft 74 has a third diameter A3. The central screw 70 has a third length L3. The third length L3 spans the entire elongated shaft 74 as well as the ball-head 72. In a preferred embodiment, the ratio between the second diameter A2 and the third diameter A3 is larger than 110:100, preferably larger than 130:100. With a large ratio between the second diameter A2 and the third diameter A3 the transfer of translational forces between the central screw 70 and the cylindrical channel 54 is enhanced.

Preferably, the ratio between the first length L1 of the expandable spinal implant assembly 1 and the third length L3 of the central screw 70 is smaller than 100:80, preferably smaller than 100:70.

The second end 75 preferably comprises a conical tip 77. The conical tip 77 has a fourth angle 81 which is substantially equal to the third inclination angle 62 of said angled slope 52 of the substantially hollow second body 40. Said conical tip 77 is intended to engage with said angled slope 52.

Figure 8B:
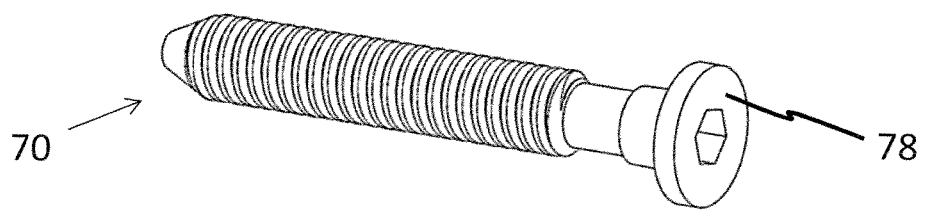
Figure 8C:
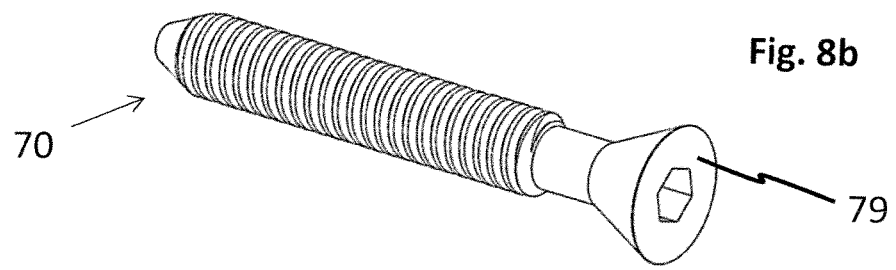
Figure 8D:
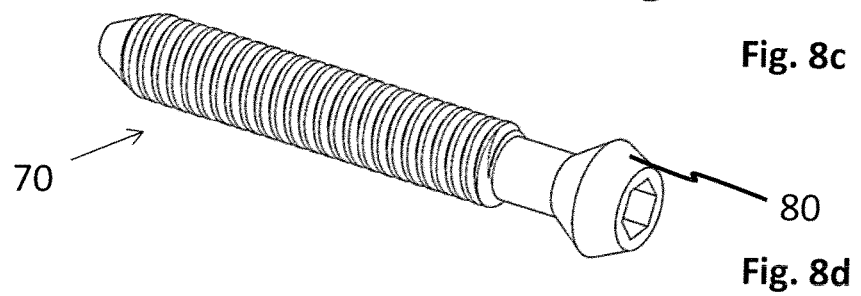

FIGS. 8b to 8d depict alternative designs of the central screw 70, namely comprising a cylindrical head 78, a conical head 79 or a double conical head 80.

FIG. 9a depicts the expandable implant assembly 1 according to the second embodiment in a first, collapsed state. The second body 40 is engaged within the first body 10. As such, the strut 17 is received within the guiding recess 53. The protrusions 47a-47z of the second body 40 are arranged within the slots 21a-21z of the first body 10. The protrusions 47a-47z and the fingers 20a-20z thereby form a flat plane defining a top face of the expandable spinal implant assembly 1. Note that the reference numerals 47a-47z, 20a-20z and 21a-21z have been omitted on FIGS. 9a to 9c for clarity reasons.

The elongated shaft 74 of the central screw 70 is engaged into the first threaded through bore 18 of the first body 10. Simultaneously, the ball head 72 of the central screw 70 is engaged and captured into the superior track 55 and the inferior track 56 forming the cylindrical channel 54 of the second body 40. The conical tip 77 of the central screw 70 engages against the angled slope 52 of the second body 40.

When a turning motion is imparted on the central screw 70, said central screw 70 is translated towards the first rear side 16 of the substantially hollow body 10, as the outer screw thread 76 is engaged with the first threaded through bore 18. This translation leads to a movement of the ball head 72 within the tracks 55, 56 of the cylindrical channel 54. As these tracks 55, 56 include an acute angle in relation to the central axis of the first threaded through bore 18, the motion of the ball head 72 along said tracks 55, 56 imparts a motion of the second body 40 relative to the first body 10.

As the strut 17 is received within the guiding recess 53 this movement is guided in a linear anterior to posterior direction.

Simultaneously, the conical tip 77 of the central screw 70 presses against the angled slope 52 hence supporting the force transfer from the linear translation of the central screw 70 to the motion of the bodies 10, 40 relative to each other.

As a result the second body 40 is pushed out of the first body 10 towards the second, expanded configuration, which is shown in FIG. 9b.

FIG. 9c shows the collapsing of the expandable spinal implant assembly 1 from the expanded configuration towards the collapsed configuration. Upon unscrewing of the central screw 70 the central screw 70 travels towards the first front side 15 of the first body 10. The ball head 72 engaged in tracks 55, 56 will hence pull the second body 40 back into the first body 10.

Figure 10:
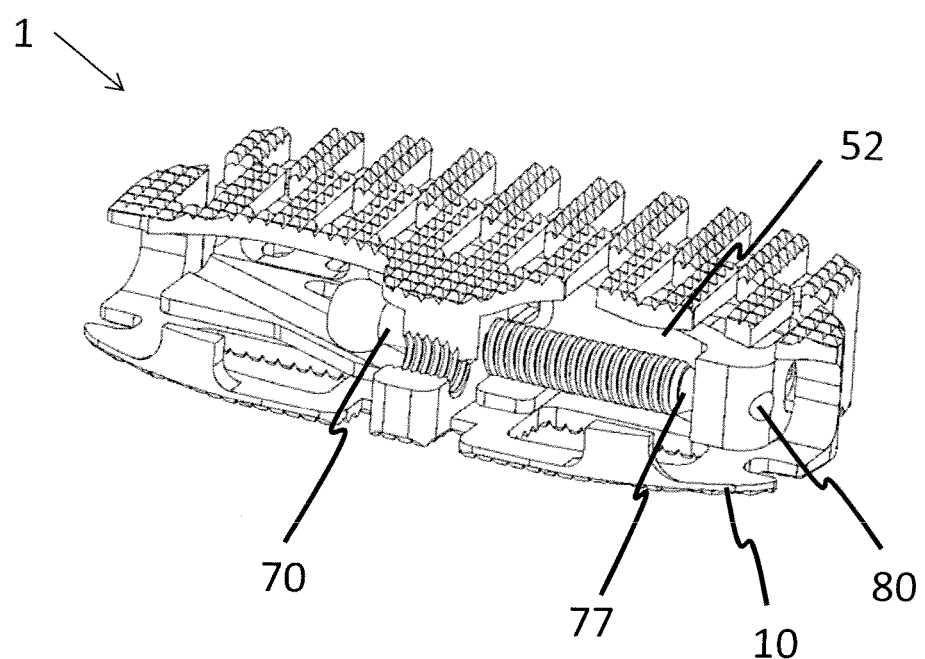
FIG. 10 an alternative embodiment of the expandable spinal implant assembly.

FIG. 10 shows an alternative embodiment of the inventive expandable spinal implant assembly 1. In this embodiment, the first body 10 comprises a cylindrical hole 80 arranged at one end of the angled slope 52. The cylindrical hole 80 is arranged such that the conical tip 77 of the central screw 70 may engage therein. Once the conical tip 77 is engaged within the cylindrical hole 80, a friction fit is established which prevents any rotational motion of the central screw 70 due to micro motion.

FIGS. 11a and 11b show an insertion instrument 100 used in connection with an expandable spinal implant assembly 1 according to the present invention. The insertion instrument 100 comprises two central channels 101, 102. The first central channel 101 is configured to guide a screwdriver 110 for actuation of the central screw 70. The second central channel 102 is intended to guide a coupling core 115. Coupling core 115 comprises a threaded tip 116 for engagement into the second threaded through bore 19 of the first body 10. The insertion instrument 100 furthermore comprises a nose 103. The nose 103 is configured to engage with recess 22 of the first body 10. By simultaneous engagement of the nose 103 into the recess 22 and the engagement of the coupling core 115 into the second threaded through bore 19, the expandable spinal implant assembly 1 is coupled to the insertion instrument 100.

Figure 12A:
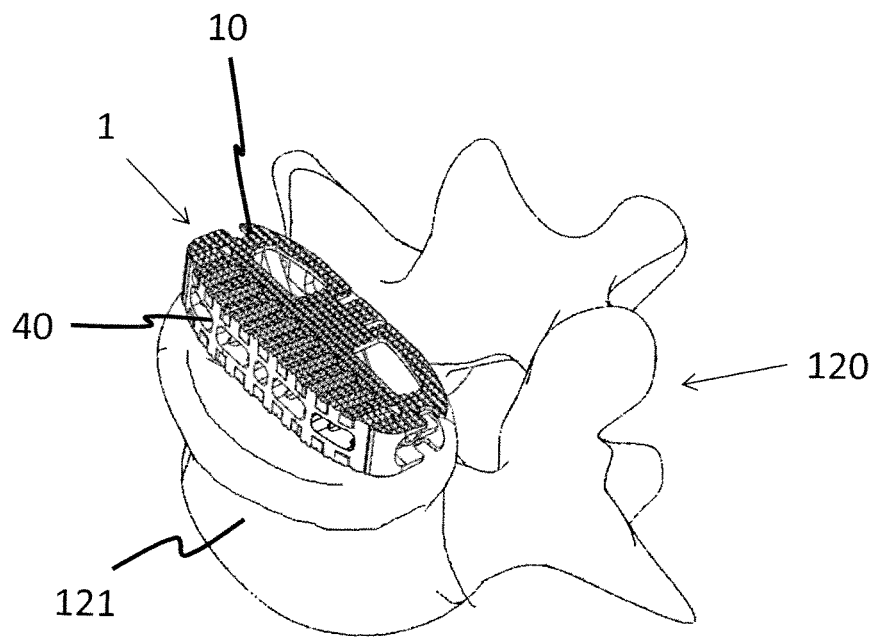
FIGS. 12a, 12b the second embodiment arranged on a vertebral body.
Figure 12B:
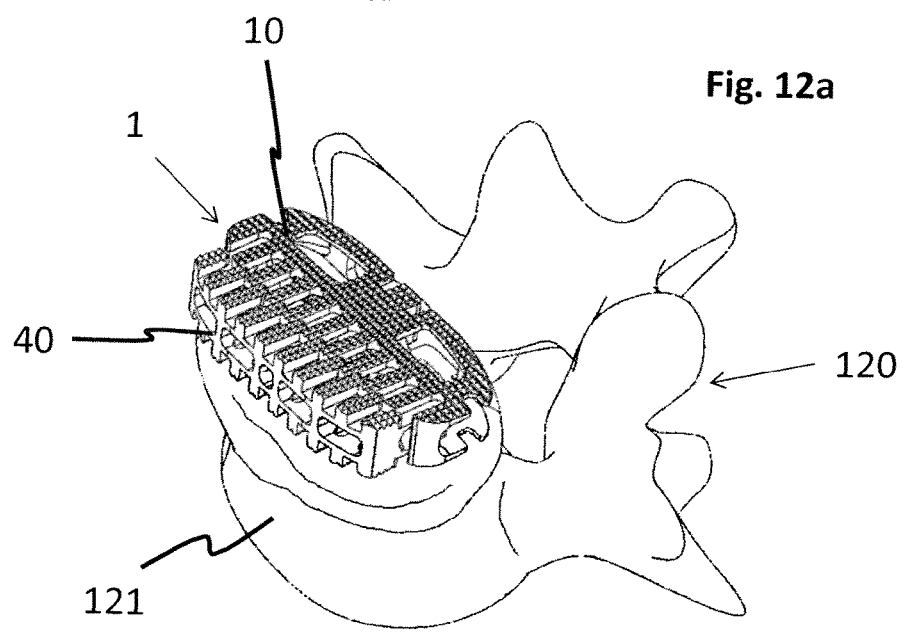

FIGS. 12a and 12b show the second embodiment of the expandable spinal implant 1 arranged on a vertebral body 121 of a target vertebra 120 in a schematic representation. For reasons of simplicity, only one vertebra 120 is shown. However, a person having skill in the art recognizes that the expandable spinal implant 1 would be arranged between two vertebrae in replacement to an intervertebral disc. FIG. 12a shows the expandable spinal implant in the first, collapsed or unexpanded configuration where the expandable spinal implant assembly 1 has a first footprint on the vertebral body 121. FIG. 12b shows the expandable spinal implant assembly 1 in the second, expanded configuration having an increased footprint on said vertebral body 121. This increased footprint is due to the relative motion of the second body 40 relative to the first body 10 in a posterior to anterior direction.

Figure 13A:
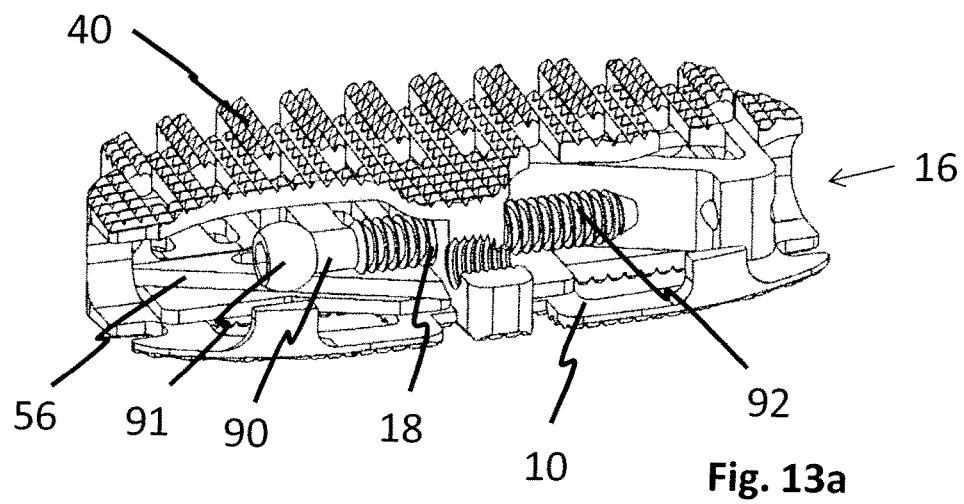
FIGS. 13a-13c a third embodiment of the expandable spinal implant assembly with a dowel.
Figure 13B:
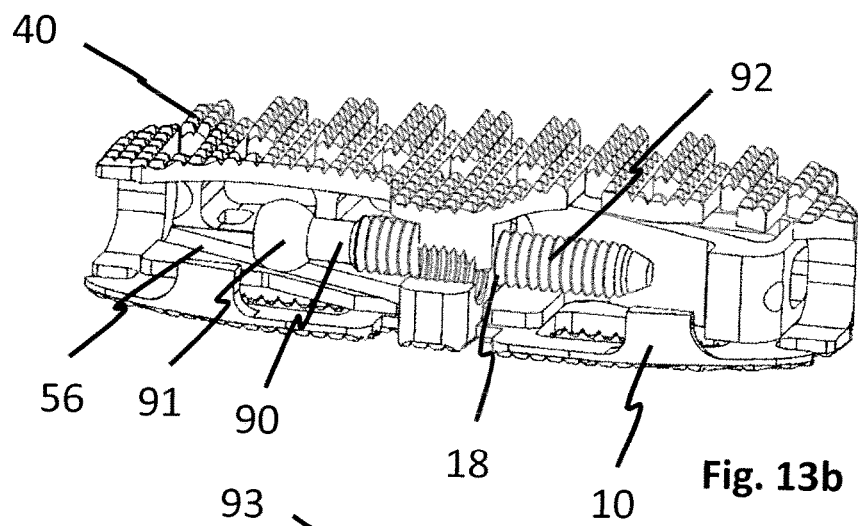
Figure 13C:
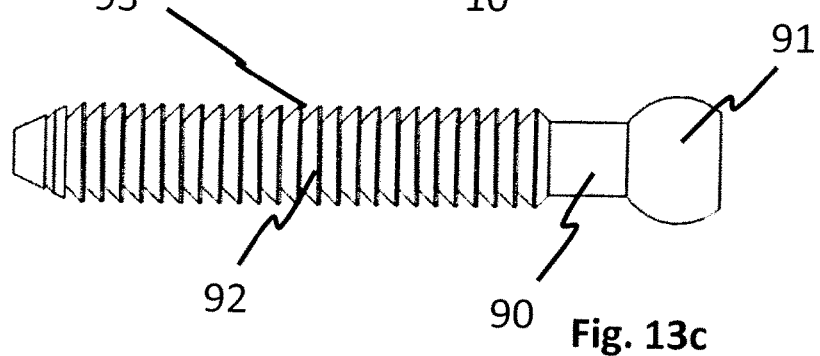
Figure 14A:
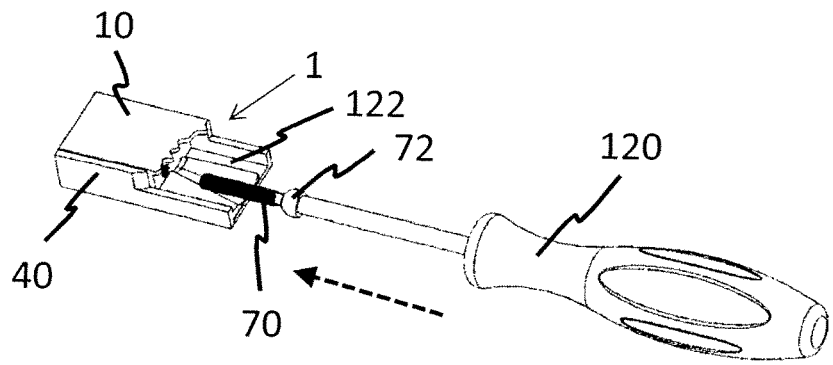
FIGS. 14a-14e another alternative embodiment of the expandable spinal implant assembly with an expansion actuating instrument.
Figure 14B:
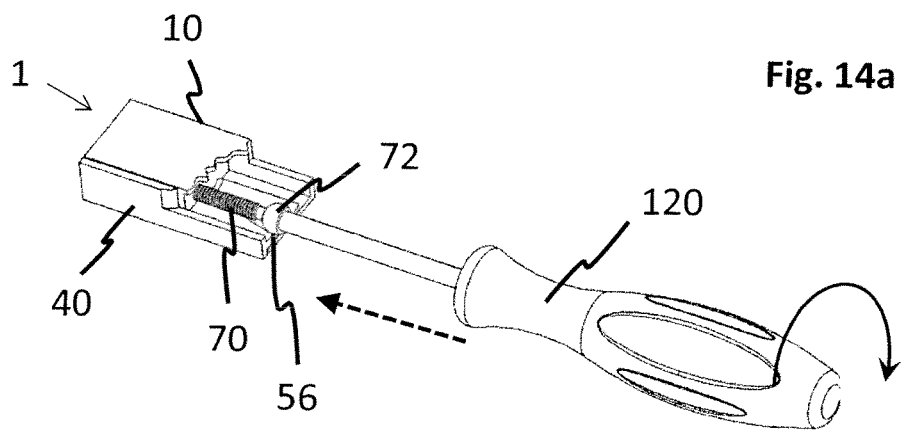
Figure 14C:
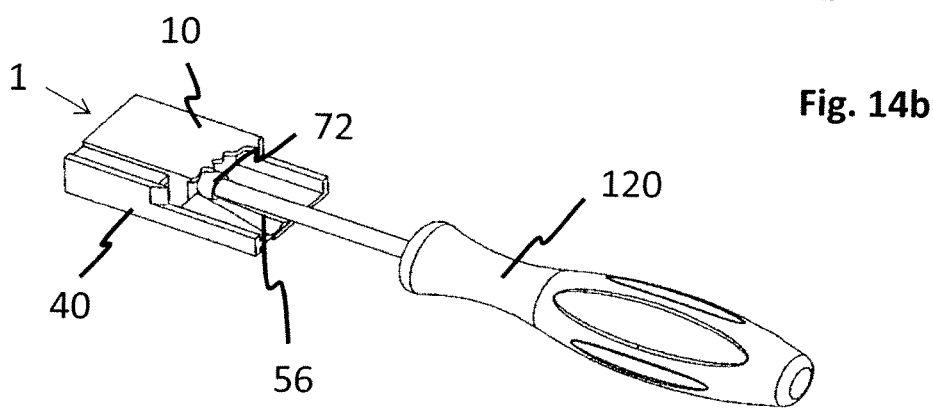
Figure 14D:
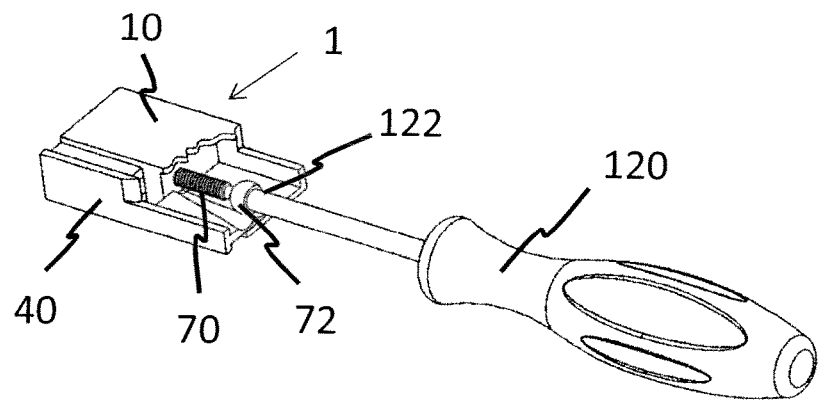
Figure 14E:
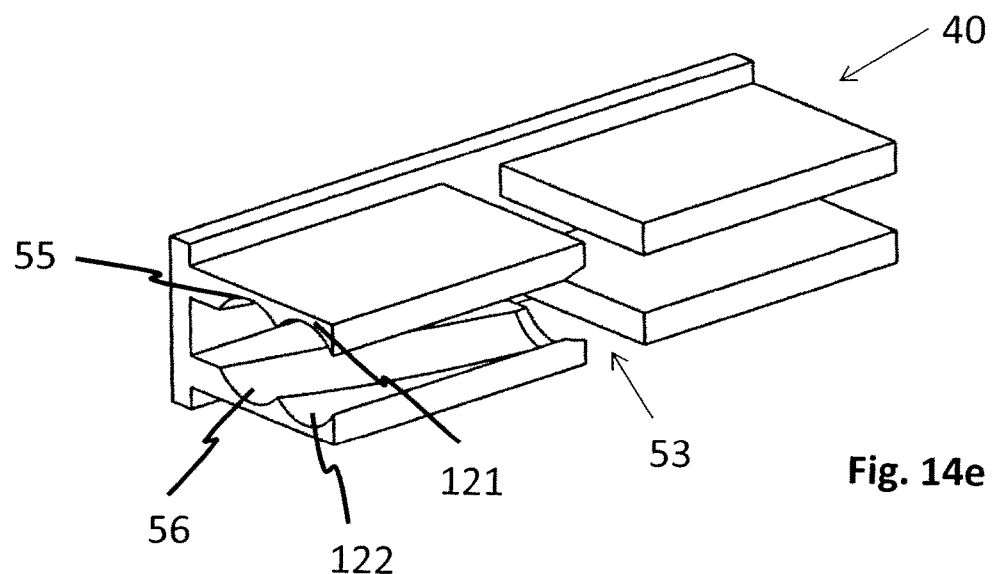

FIGS. 13a to 13c show a third embodiment of the expandable spinal implant assembly 1, in which the central screw 70 is replaced by a dowel 90. The dowel 90 comprises a dowel head 91 which is engageable in the tracks 55, 56 as well as a saw teeth structure 92 on an elongate dowel body 93. The saw teeth structure 92 is chosen such that a translation of the dowel 90 through the first threaded through hole 18 towards the first rear side 16 of the first body 10 is possible, while a reverse motion is prevented by the interaction of the saw teeth structure 92 with the rim of the first through hole 18.

FIGS. 14a-14e show another alternative embodiment of the expandable spinal implant assembly 1. The expansion screw is replaced by an expansion actuating instrument 120. The expansion actuating instrument 120 is used to expand the expandable spinal implant assembly 1 and is then removed. In order to facilitate the possibility to remove the instrument, the superior track 55 and an inferior track 56 of the second body 40 intersect with a second superior track 121 and a second inferior track 122. Second superior track 121 and a second inferior track 122 are oriented parallel to the axis of said first threaded through bore 18 of the first implant body 10. When the expandable spinal implant assembly 1 has reached the expanded configuration, the expansion actuating instrument 120 can be removed without causing the expandable spinal implant assembly to collapse by translating the expansion actuating instrument 120 through the second tracks 121, 122.

FIGS. 15a and 15b show a further embodiment of the expandable spinal implant assembly 1. The strut 17 of the first body 10 comprises a first portion 130 connecting the first top inside face of the superior endplate 11 with the first bottom inside face of the inferior endplate 12 and a second cylindrical portion 131 extending therefrom. The first threaded through bore 18 is located in said second cylindrical portion 131.

The second body 40 comprises a guiding bore 132 which is aligned with the guiding recess 53. Both the first body 10 and the second body 40 have complementary, essentially V-shaped sides which match together when the expandable spinal implant assembly 1 is in the first, unexpanded configuration.

The second cylindrical portion 131 is inserted into the guiding bore 132. Hence, in this embodiment, the translation of the first body 10 relative to the second body 40 from the first, unexpanded configuration to the second, expanded configuration is additionally guided by the interaction of the second cylindrical portion 131 of the strut 17 with said guiding bore 132.

The central screw 70 is engaged with the first threaded through bore 18, wherein the ball head 72 is engaged within the cylindrical channel 54 arranged within said second body 40. Such as to allow the insertion of the central screw 70 into said expandable spinal implant assembly 1, a partial round opening 133 is provided on the first front side 15 of the first body 10.

Further, the second threaded through bore 19 is provided on the first front side 15 of the first body 10. The second threaded through bore 19 allows the coupling of the expandable spinal implant 1 with an insertion instrument.

The invention claimed is:

1. An expandable spinal implant assembly for insertion between two adjacent vertebral bodies, comprising:
   a) a substantially hollow first body with a first superior endplate with a first top inside face and a first inferior endplate with a first bottom inside face, said first superior endplate and said first inferior endplate being connected together on at least one side by a lateral wall;
   b) at least one strut being arranged within said first body and connecting the first top inside face of said superior endplate with the first bottom inside face of said inferior endplate, said strut comprising a first threaded through bore with a central axis;

c) a substantially hollow second body with a second superior endplate and a second inferior endplate, said second body being at least partially inserted within said first body;

d) a central screw with a first end comprising a ball-head and a drive, said central screw further having a threaded shaft which is engaged within said first threaded through bore, wherein at least one track is arranged on a second top inside face of said second superior endplate and/or on a second bottom inside face of said second inferior endplate, said at least one track being oriented at an acute angle relative to the central axis of said first threaded through bore when said substantially hollow second body is at least partially inserted into said substantially hollow first body and wherein said ball-head of said central screw is engaged into said at least one track.

2. The expandable spinal implant assembly according to claim 1, wherein said expandable spinal assembly includes a superior track located on said second top inside face of said second superior endplate and an inferior track located on said second lower inside face of said second inferior endplate, said superior track and said inferior track—being arranged symmetrically to each other and forming a cylindrical channel.

3. The expandable spinal implant assembly according to claim 1, wherein the acute angle of said at least one track relative to said central axis of the first threaded through bore is between 5° and 45°, preferably between 10° and 30°.

4. The expandable spinal implant assembly according to claim 1, wherein said first body comprises at least one slot and said second body comprises at least one protrusion, wherein said at least one protrusion is configured to engage with said at least one slot and said at least on protrusion substantially extends to said first superior endplate and to said first inferior endplate, said at least one protrusion preferably being flush with said first superior endplate and with said first inferior endplate.

5. The expandable spinal implant assembly according to claim 1, wherein said first top inside face and said first bottom inside face are spaced from each other by a first distance D1 and are substantially parallel to each other and wherein said second superior endplate and said second inferior endplate are substantially parallel to each and are spaced from each other by a second distance D2 which is smaller than said first distance D1.

6. The expandable spinal implant assembly according to claim 1, wherein said ball head of said central screw is a cylindrical head, a conical head or a double conical head.

7. The expandable spinal implant assembly according to claim 1, wherein said second body comprises at least one second track arranged on a second top inside face of said second superior endplate and/or on a second bottom inside face of said second inferior endplate, said at least one second track being oriented parallel relative to the central axis of said first through bore.

8. The expandable spinal implant assembly according to claim 1, wherein said ball head has a second diameter and said elongated shaft has a third diameter, wherein the ratio between said second diameter and said third diameter is at least 110:100, preferably at least 130:100.

9. The expandable spinal implant assembly according to any of claim 1, wherein the expandable spinal implant assembly has a first footprint in the first, unexpanded configuration and a second footprint in the second, expanded configuration, wherein the ratio between said first footprint and said second footprint is at least 100:125.

10. The expandable spinal implant assembly according to claim 1, wherein said spinal implant assembly has a first length L1 and said central screw has a third length L3, wherein the ratio between said first length L1 and said third length L3 is smaller than 100:80, preferably smaller than 100:70.

11. The expandable spinal implant assembly according to claim 1, wherein said first element said second element and said central screw are made of titanium, a titanium allow, stainless steel or a biocompatible polymer, preferably polyetheretherketone.

\* \* \* \* \*